US005620994A

United States Patent [19]

Naito et al.

[11] Patent Number: 5,620,994

[45] Date of Patent: Apr. 15, 1997

[54] AZOLYLAMINE DERIVATIVE

[75] Inventors: Takanobu Naito; Haruhito Kobayashi; Hironobu Ogura; Kiyoshi Nagai; Tokiko Nishida; Tadashi Arika; Mamoru Yokoo; Satoko Shusse, all of Kyoto, Japan

[73] Assignee: Kaken Pharmaceutical Co., Ltd., Tokyo, Japan

[21] Appl. No.: 532,800

[22] Filed: Nov. 7, 1995

[30] Foreign Application Priority Data

May 10, 1993 [JP] Japan .................................... 5-132931

[51] Int. Cl.$^6$ ...................... A61K 31/445; C07D 401/06; C07D 403/06

[52] U.S. Cl. .......................... 514/326; 514/212; 514/383; 540/603; 546/210; 548/267.2; 548/267.8

[58] Field of Search ............................ 540/603; 546/210; 548/267.2, 267.8; 514/212, 326, 383

[56] References Cited

U.S. PATENT DOCUMENTS 4,507,484 3/1985 Gymer et al. .

FOREIGN PATENT DOCUMENTS

0054974A1 6/1982 European Pat. Off. .
2159148 11/1985 United Kingdom .

*Primary Examiner*—Patricia L. Morris
*Attorney, Agent, or Firm*—Armstrong, Westerman, Hattori, McLeland & Naughton

[57] ABSTRACT

There is disclosed a fungicide containing, effective ingredient, a compound having the general formula (I):

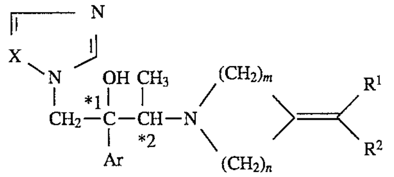

(I)

or an acid addition salt thereof, particularly the compound wherein an absolute configuration of the asymmetric carbon atoms is R,R-configuration or an acid addition salt thereof.

12 Claims, No Drawings

AZOLYLAMINE DERIVATIVE

TECHNICAL FIELD

The present invention relates to an azolylamine derivative which is effective for treatment for mycosis in human and animals and useful as fungicides for agricultural and horticultural use or industrial use.

BACKGROUND ART

Azolylamine derivatives having, in the molecule, both of an azolyl group such as triazolyl group or imidazolyl group and a cyclic amino group such as piperidino group, pyrrolidino group or morpholino group are described in JP-A(Japanese Unexamined Patent Publication)-140768/1982 and GB-A-2159148. However, it is hard to say in the aspect of an antifungal action etc. that each compound has sufficient efficacy as a medicament. Furthermore, any compound having methylene group or a substituted methylene group on the cyclic amino group is not disclosed therein.

The present invention provides a novel azolylamine derivative showing the potent antifungal activity which is characterized by having methylene group or a substituted methylene group on the cyclic amino group.

DISCLOSURE OF THE INVENTION

The present invention provides a compound having the general formula (I):

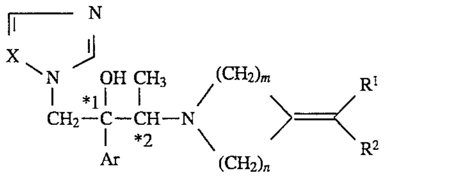

(I)

wherein

- Ar is non-substituted phenyl group or a phenyl group substituted with 1 to 3 substituents selected from a halogen atom and trifluoromethyl,
- $R^1$ and $R^2$ are the same or different and are hydrogen atom, a lower alkyl group, a non-substituted aryl group, an aryl group substituted with 1 to 3 substituents selected from a halogen atom and a lower alkyl group, an alkenyl group, an alkynyl group or an aralkyl group,
- m is 2 or 3,
- n is 1 or 2,
- X is nitrogen atom or CH, and
- *1 and *2 mean an asymmetric carbon atom, or an acid addition salt thereof.

As the above-mentioned compound having the general formula (I), there are particularly preferable the compound wherein an absolute configuration of the asymmetric carbon atoms with *1 and *2 is R,R-configuration, and the compound being a mixture containing the compound having the general formula (I) wherein the absolute configuration of the asymmetric carbon atoms with *1 and *2 is R,R-configuration or an acid addition salt thereof and other optical isomer.

The present invention also provides a fungicide containing the above-mentioned compound having the general formula (I) or an acid addition salt thereof as an effective ingredient, and a process for treating mycosis using the above-mentioned compound.

BEST MODE FOR CARRYING OUT THE INVENTION

In the above-mentioned general formula (I), the substituted phenyl group is a phenyl group having 1 to 3 substituents selected from a halogen atom and trifluoromethyl, and includes, for instance, 2,4-difluorophenyl, 2,4-dichlorophenyl, 4-fluorophenyl, 4-chlorophenyl, 2-chlorophenyl, 4-trifluoromethylphenyl, 2-chloro-4-fluorophenyl, 4-bromophenyl or the like.

The lower alkyl group includes, for instance, a straight chain, branched chain or cyclic alkyl group having 1 to 6 carbon atoms such as methyl, ethyl, n-propyl, isopropyl, n-butyl, isobutyl, sec-butyl, tert-butyl, n-pentyl, isopentyl, neopentyl and tert-pentyl.

The non-substituted aryl group includes, for instance, phenyl, naphthyl, biphenyl, or the like.

The substituted aryl group includes, for instance, 2,4-difluorophenyl, 2,4-dichlorophenyl, 4-fluorophenyl, 4-chlorophenyl, 2-chlorophenyl, 4-trifluoromethylphenyl, 2-chloro-4-fluorophenyl, 4-bromophenyl, 4-tert-butylphenyl, 4-nitrophenyl, or the like.

The alkenyl group includes, for instance, vinyl, 1-propenyl, styryl, or the like. The alkynyl group includes, for instance, ethynyl, or the like.

The aralkyl group includes, for instance, benzyl, naphthylmethyl, 4-nitrobenzyl, or the like.

The compound of the present invention having the general formula (I) contains at least two asymmetric carbon atoms in the molecule, and there exsist an optical isomer and a diastereomer. With respect to the optical isomer, both enantiomers can be obtained according to the general procedure of optical resolution or asymmetric synthesis. A separation of the diastereomer can be carried out according to the usual separation procedure such as a fractional recrystallization or a chromatography to give each isomer. The compound having the general formula (I) includes one of these isomers or a mixture thereof.

Among these, the compound wherein an absolute configuration of the asymmetric carbon atoms is R,R-configuration, has particularly potent antifungal action and therefore it is preferably used particularly.

Representative examples of the compound of the present invention having the general formula (I) include, for instance, (2R,3R)-2-(2,4-difluorophenyl)-3-(4-methylenepiperidine-1-yl)-1-(1H-1,2,4-triazole-1-yl)butane-2-ol,
(2S,3S)-2-(2,4-difluorophenyl)-3-(4-methylenepiperidine-1-yl)-1-(1H-1,2,4-triazole-1-yl)butane-2-ol,
(2RS,3RS)-2-(2,4-difluorophenyl)-3-(4-methylenepiperidine-1-yl)-1-(1H-1,2,4-triazole-1-yl)butane-2-ol,
(2R,3R)-2-(2,4-difluorophenyl)-3-(4-methylenepiperidine-1-yl)-1-(1H-imidazole-1-yl)butane-2-ol,
(2S,3S)-2-(2,4-difluorophenyl)-3-(4-methylenepiperidine-1-yl)-1-(1H-imidazole-1-yl)butane-2-ol,
(2RS,3RS)-2-(2,4-difluorophenyl)-3-(4-methylenepiperidine-1-yl)-1-(1H-imidazole-1-yl)butane-2-ol,
(2R,3R)-2-(4-chlorophenyl)-3-(4-methylenepiperidine-1-yl)-1-(1H-1,2,4-triazole-1-yl)butane-2-ol,
(2S,3S)-2-(4-chlorophenyl)-3-(4-methylenepiperidine-1-yl)-1-(1H-1,2,4-triazole-1-yl)butane-2-ol,
(2RS,3RS)-2-(4-chlorophenyl)-3-(4-methylenepiperidine-1-yl)-1-(1H-1,2,4-triazole-1-yl)butane-2-ol,
(2R,3R)-2-(4-chlorophenyl)-3-(4-methylenepiperidine-1-yl)-1-(1H-imidazole-1-yl)butane-2-ol, (2S,3S)-2-(4-chlorophenyl)-3-(4-methylenepiperidine-1-yl)-1-(1H-imidazole-1-yl)butane-2-ol, (2RS,3RS)-2-(4-chlorophenyl)-3-(4-methylenepiperidine-1-yl)-1-(1H-imidazole-1-yl)butane-2-ol, (2R,3R)-2-(4-trifluoromethylphenyl)-3-(4-methylenepiperidine-1-yl)-1-(1H-1,2,4-triazole-1-yl)butane-2-ol, (2S,3S)-2-(4-trifluoromethylphenyl)-3-(4-methylenepiperidine-1-yl)-1-(1H-1,2,4-triazole-1-yl)butane-2-ol, (2RS,3RS)-2-(4-trifluoromethylphenyl)-3-(4-methylenepiperidine-1-yl)-1-(1H-1,2,4-triazole-1-yl)butane-2-ol, (2R,3R)-2-(4-trifluoromethylphenyl)-3-(4-methylenepiperidine-1-yl)-1-(1H-imidazole-1-yl)butane-2-ol, (2S,3S)-2-(4-trifluoromethylphenyl)-3-(4-methylenepiperidine-1-yl)-1-(1H-imidazole-1-yl)butane-2-ol, (2RS,3RS)-2-(4-trifluoromethylphenyl)-3-(4-methylenepiperidine-1-yl)-1-(1H-imidazole-1-yl)butane-2-ol, (2R,3R)-2-(2,4-dichlorophenyl)-3-(4-methylenepiperidine-1-yl)-1-(1H-1,2,4-triazole-1-yl)butane-2-ol, (2S,3S)-2-(2,4-dichlorophenyl)-3-(4-methylenepiperidine-1-yl)-1-(1H-1,2,4-triazole-1-yl)butane-2-ol, (2RS,3RS)-2-(2,4-dichlorophenyl)-3-(4-methylenepiperidine-1-yl)-1-(1H-1,2,4-triazole-1-yl)butane-2-ol, (2R,3R)-2-(2,4-dichlorophenyl)-3-(4-methylenepiperidine-1-yl)-1-(1H-imidazole-1-yl)butane-2-ol, (2S,3S)-2-(2,4-dichlorophenyl)-3-(4-methylenepiperidine-1-yl)-1-(1H-imidazole-1-yl)butane-2-ol, (2RS,3RS)-2-(2,4-dichlorophenyl)-3-(4-methylenepiperidine-1-yl)-1-(1H-imidazole-1-yl)butane-2-ol, (2R,3R)-2-(2,4-difluorophenyl)-3-(4-ethylidenepiperdine-1-yl)-1-(1H-1,2,4-triazole-1-yl)butane-2-ol, (2S,3S)-2-(2,4-difluorophenyl)-3-(4-ethylidenepiperdine-1-yl)-1-(1H-1,2,4-triazole-1-yl)butane-2-ol, (2RS,3RS)-2-(2,4-difluorophenyl)-3-(4-ethylidenepiperdine-1-yl)-1-(1H-1,2,4-triazole-1-yl)butane-2-ol, (2R,3R)-2-(2,4-difluorophenyl)-3-(4-propylidenepiperdine-1-yl)-1-(1H-1,2,4-triazole-1-yl)butane-2-ol, (2S,3S)-2-(2,4-difluorophenyl)-3-(4-propylidenepiperdine-1-yl)-1-(1H-1,2,4-triazole-1-yl)butane-2-ol, (2RS,3RS)-2-(2,4-difluorophenyl)-3-(4-propylidenepiperdine-1-yl)-1-(1H-1,2,4-triazole-1-yl)butane-2-ol, (2R,3R)-2-(2,4-difluorophenyl)-3-(4-n-butylidenepiperdine-1-yl)-1-(1H-1,2,4-triazole-1-yl)butane-2-ol, (2S,3S)-2-(2,4-difluorophenyl)-3-(4-n-butylidenepiperdine-1-yl)-1-(1H-1,2,4-triazole-1-yl)butane-2-ol, (2RS,3RS)-2-(2,4-difluorophenyl)-3-(4-n-butylidenepiperdine-1-yl)-1-(1H-1,2,4-triazole-1-yl)butane-2-ol, (2R,3R)-2-(2,4-difluorophenyl)-3-(4-n-pentylidenepiperdine-1-yl)-1-(1H-1,2,4-triazole-1-yl)butane-2-ol, (2S,3S)-2-(2,4-difluorophenyl)-3-(4-n-pentylidenepiperdine-1-yl)-1-(1H-1,2,4-triazole-1-yl)butane-2-ol, (2RS,3RS)-2-(2,4-difluorophenyl)-3-(4-n-pentylidenepiperdine-1-yl)-1-(1H-1,2,4-triazole-1-yl)butane-2-ol, (2R,3R)-2-(2,4-difluorophenyl)-3-(4-n-hexylidenepiperdine-1-yl)-1-(1H-1,2,4-triazole-1-yl)butane-2-ol, (2S,3S)-2-(2,4-difluorophenyl)-3-(4-n-hexylidenepiperdine-1-yl)-1-(1H-1,2,4-triazole-1-yl)butane-2-ol, (2RS,3RS)-2-(2,4-difluorophenyl)-3-(4-n-hexylidenepiperdine-1-yl)-1-(1H-1,2,4-triazole-1-yl)butane-2-ol, (2R,3R)-2-(2,4-difluorophenyl)-3-(4-cyclopropylmethylene-piperdine-1-yl)-1-(1H-1,2,4-triazole-1-yl)butane-2-ol, (2S,3S)-2-(2,4-difluorophenyl)-3-(4-cyclopropylmethylenepiperdine-1-yl)-1-(1H-1,2,4-triazole-1-yl)butane-2-ol, (2RS,3RS)-2-(2,4-difluorophenyl)-3-(4-cyclopropylmethylenepiperdine-1-yl)-1-(1H-1,2,4-triazole-1-yl)butane-2-ol, (2R,3R)-2-(2,4-difluorophenyl)-3-(4-cyclohexylmethylenepiperdine-1-yl)-1-(1H-1,2,4-triazole-1-yl)butane-2-ol, (2S,3S)-2-(2,4-difluorophenyl)-3-(4-cyclohexylmethylenepiperdine-1-yl)-1-(1H-1,2,4-triazole-1-yl)butane-2-ol, (2RS,3RS)-2-(2,4-difluorophenyl)-3-(4-cyclohexylmethylenepiperdine-1-yl)-1-(1H-1,2,4-triazole-1-yl)butane-2-ol, (2R,3R)-2-(2,4-difluorophenyl)-3-(4-benzylidenepiperdine-1-yl)-1-(1H-1,2,4-triazole-1-yl)butane-2-ol, (2S,3S)-2-(2,4-difluorophenyl)-3-(4-benzylidenepiperdine-1-yl)-1-(1H-1,2,4-triazole-1-yl)butane-2-ol, (2RS,3RS)-2-(2,4-difluorophenyl)-3-(4-benzylidenepiperdine-1-yl)-1-(1H-1,2,4-triazole-1-yl)butane-2-ol, (2R,3R)-2-(2,4-difluorophenyl)-3-(4-isopropylidenepiperdine-1-yl)-1-(1H-1,2,4-triazole-1-yl)butane-2-ol, (2S,3S)-2-(2,4-difluorophenyl)-3-(4-isopropylidenepiperdine-1-yl)-1-(1H-1,2,4-triazole-1-yl)butane-2-ol, (2RS,3RS)-2-(2,4-difluorophenyl)-3-(4-isopropylidenepiperdine-1-yl)-1-(1H-1,2,4-triazole-1-yl)butane-2-ol, (2R,3R)-2-(2,4-difluorophenyl)-3-(4-diphenylmethylenepiperdine-1-yl)-1-(1H-1,2,4-triazole-1-yl)butane-2-ol, (2S,3S)-2-(2,4-difluorophenyl)-3-(4-diphenylmethylenepiperdine-1-yl)-1-(1H-1,2,4-triazole-1-yl)butane-2-ol, (2RS,3RS)-2-(2,4-difluorophenyl)-3-(4-diphenylmethylenepiperdine-1-yl)-1-(1H-1,2,4-triazole-1-yl)butane-2-ol, (2R,3R)-2-(2,4-difluorophenyl)-3-(4-propenylidenepiperdine-1-yl)-1-(1H-1,2,4-triazole-1-yl)butane-2-ol, (2S,3S)-2-(2,4-difluorophenyl)-3-(4-propenylidenepiperdine-1-yl)-1-(1H-1,2,4-triazole-1-yl)butane-2-ol, (2RS,3RS)-2-(2,4-difluorophenyl)-3-(4-propenylidenepiperdine-1-yl)-1-(1H-1,2,4-triazole-1-yl)butane-2-ol, (2R,3R)-2-(2,4-difluorophenyl)-3-(4-propynylidenepiperdine- 1-yl)-1-(1H-1,2,4-triazole-1-yl)butane-2-ol, (2S,3S)-2-(2,4-difluorophenyl)-3-(4-propynylidenepiperdine-1-yl)-1-(1H-1,2,4-triazole-1-yl)butane-2-ol, (2RS,3RS)-2-(2,4-difluorophenyl)-3-(4-propynylidenepiperdine-1-yl)-1-(1H-1,2,4-triazole-1-yl)butane-2-ol, (2R,3R)-2-(2,4-difluorophenyl)-3-(3-methylenepiperidine-1-yl)-1-(1H-1,2,4-triazole-1-yl)butane-2-ol, (2S,3S)-2-(2,4-difluorophenyl)-3-(3-methylenepiperidine-1-yl)-1-(1H-1,2,4-triazole-1-yl)butane-2-ol, (2RS,3RS)-2-(2,4-difluorophenyl)-3-(3-methylenepiperidine-1-yl)-1-(1H-1,2,4-triazole-1-yl)butane-2-ol, (2R,3R)-2-(2,4-difluorophenyl)-3-(3-methylenepyrrolidine-1-yl)-1-(1H-1,2,4-triazole-1-yl)butane-2-ol, (2S,3S)-2-(2,4-difluorophenyl)-3-(3-methylenepyrrolidine-1-yl)-1-(1H-1,2,4-triazole-1-yl)butane-2-ol, (2RS,3RS)-2-(2,4-difluorophenyl)-3-(3-methylenepyrrolidine-1-yl)-1-(1H-1,2,4-triazole-1-yl)butane-2-ol, and the like.

The compound of the present invention having the general formula (I) can be prepared according to the process shown as below:

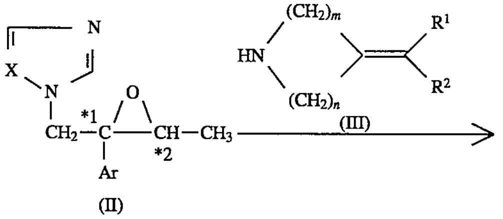

(II)

-continued

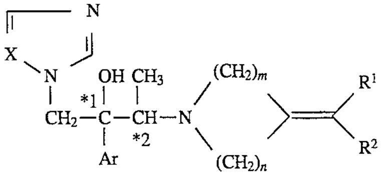

(I)

(In the above-mentioned formulae, Ar, $R^1$, $R^2$, X, m and n have the same meanings as defined above.)

Namely, the reaction of an epoxy compound having the general formula (II) and an amine derivative having the general formula (III) can lead to the compound having the general formula (I).

The epoxy compound having the general formula (II) can be obtained according to such process as is described in JP-A(Japanese Unexamined Patent Publication)-19 1262/1990 etc., for example, a process wherein a compound having the general formula (IV);

(IV)

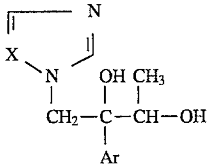

wherein Ar and X have the same meanings as defined above, is reacted in the presence of a base with a compound having the formula $R^3SO_2$—O—$SO_2R^3$ or $R^3SO_2$—Z, wherein $R^3$ is a lower alkyl group, a halogenated lower alkyl group, or a phenyl group which may be substituted, and Z is a leaving group such as a halogen atom, to give a compound (V):

(V)

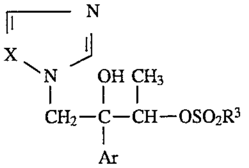

and then the compound (V) is reacted with a base.

The amine derivative having the general formula (III) can be obtained according to the known synthetic process described in, for example, Chem. Pharm. Bull 41 (11) 1971–1986 (1993) or processes described in Reference Examples of the present invention.

In case that the amine derivative is in a form of a salt thereof with an acid such as a base, the amine derivative is used in a form of a free amine by being neutralized previously or in a reaction solution with an inorganic base such as sodium hydroxide or an organic base such as triethylamine.

The reaction is usually carried out using water, an organic solvent or a mixed solution of water and an organic solvent, or in the absence of any solvent. As the organic solvent, a solvent which does not react with a starting compound can be used. For example, an alcohol such as methanol, ethanol, n-propanol, isopropanol, n-butanol, tert-butanol, ethylene glycol, propylene glycol, grycerin or methyl cellosolve, an ether such as tetrahydrofuran, dioxane or dimethoxyethane, an amide such as N,N-dimethylformamide or N,N-dimethylacetamide, dimethyl sulfoxide, and the like can be used alone or in a mixture thereof.

In the above-mentioned reaction system, the reaction advances more smoothly by adding 1 to 80 v/v % of water in the mixed solution to the reaction system in comparison with using only an organic solvent.

With respect to an amount of each material in the reaction solution, from 1 to 20 mol of the compound (III) is used per mol of the compound (II).

A reaction temperature is room temperature to 200° C., preferably 50° to 150° C. A reaction time is 1 to 72 hours.

After the end of the reaction, the solvent is removed and then purification is carried out according to a procedure such as a recrystallization or a chromatography. Thereby the compound of the present invention having the general formula (I) is isolated.

The compound of the present invention having the general formula (I) can, if required, form a pharmaceutically acceptable salt thereof, for example, a salt thereof with an inorganic acid such as hydrochloric acid, sulfuric acid, nitric acid, phosphoric acid or hydrobromic acid, and a salt thereof with an organic acid such as fumaric acid, maleic acid, acetic acid, malic acid, tartaric acid, citric acid, methanesulfonic acid or toluenesulfonic acid.

Then, the antifungal activity of the compound of the present invention having the above-mentioned general formula (I) is described. Test compound number used in the following tests was referred to the example number described below.

1. Determination of the minimum inhibitory concentration (MIC)

MIC of a test compound against *Candida albicans* ATCC-10259 was determined by the both dilution method employing synthetic amino acid medium (SAAMF medium). Namely, to 3 μl of twofold dilution series of solution containing the test compound was added 300 μl of SAAMF medium inoculated with the fungus at the final concentration of $1\times10^3$ a cells/ml. After thus obtained mixture was incubated at 35° C. for 2 days, MIC was determined by examining a minimum concentration of the test compound in which concentration the test compound inhibited the growth of the fungus. MIC of a test compound against the fungus other than the *Candida albicans* was determined by the agar dilution method employing Sabouraud's agar medium. That is to say, a test compound was dissolved in dimethyl sulfoxide to give a solution containing the test compound in the concentration of 10 mg/ml. Further, thus obtained solution was diluted with dimethyl sulfoxide according to two-fold dilution series and 0.1 ml of the diluted solution was taken into a sterile shale. After 9.9 ml of Sabouraud's agar medium was added thereto, the mixture was sufficiently mixed to give a drug-added plate. The plate was inoculated with 5 μl of a fungus suspension at $10^6$ cells/ml by Microplanter (Sakuma Seisakusho Co., Ltd.). As to *Aspergillus fumigatus* NI-5561 and *Cryptococcus neoformans* NI-7496, a plate was incubated at 30° C. for 48 hours. As to *Trichophyton mentagrophytes* KD-01, a plate was incubated at 30° C. for 7 days. After incubation, MIC was determined by examining a minimum concentration of a test compound in which concentration the test compound inhibited the growth of the fungus. The results thereof are shown in Table 1. Clotrimazole and fluconazole were used as comparative control compounds.

The abbreviated designation of names of the test fungi is as follows:

| Name of fungus | Abbreviated designation |
|---|---|
| *Candida albicans* ATCC 10259 | C.a. |
| *Cryptococcus neoformans* NI-7496 | Cr.n. |
| *Aspergillus fumigatus* NI-5561 | A.f. |
| *Trichophyton mentagrophytes* KD-01 | T.m. |

The antifungal activity (the minimum inhibitory concentration MIC) of the compound of the present invention in the Examples against each fungus is shown in Table 1.

TABLE 1

| Test compound | Minimum inhibitory concentration (MIC (μg/ml) Test fungus | | | |
|---|---|---|---|---|
| (Ex. No.) | C.a. | Cr.n. | A.f. | T.m. |
| 1 | <0.025 | 0.05 | 0.05 | 0.39 |
| 2 | <0.025 | 0.1 | 0.1 | 0.39 |
| 3 | 0.39 | 0.78 | >100 | 50 |
| 4 | <0.025 | <0.025 | 0.05 | <0.025 |
| 5 | <0.025 | 0.025 | 0.05 | 0.1 |
| 6 | <0.0125 | 0.2 | 6.25 | 3.13 |
| 7 | 0.025 | 0.05 | 0.39 | 0.39 |
| 8 | <0.025 | 0.1 | 0.2 | 0.78 |
| 10 | <0.025 | 0.025 | 0.1 | 0.39 |
| 12 | <0.025 | 0.1 | 0.2 | 0.78 |
| 13 | 0.1 | 0.39 | 0.78 | 1.56 |
| 14 | <0.025 | 0.39 | 0.39 | 0.78 |
| Clotrimazole | 0.025 | 0.2 | 0.78 | 0.39 |
| Fluconazole | 0.39 | 12.5 | >100 | >100 |

Clotrimazole

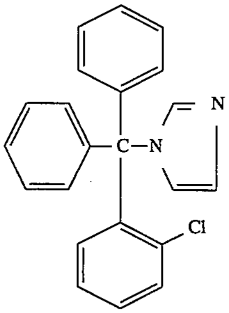

Fluconazole

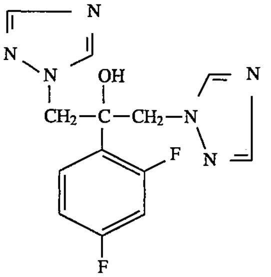

The above-mentioned results reveal that the compound of the present invention having the general formula (I), especially the compound wherein the absolute configuration is R,R-configuration, has extremely high activity in comparison with conventional fungicides.

Furthermore, compared to Clotrimazole and fluconazole, it is found that the compound of the present invention, i.e. the compound wherein a cyclic amino group having methylene group is bonded, has surprisingly high activity.

2. Test on treatment for infection (1) Effect on trichophytosis in guinea pigs.

In the back of male Hartley guinea pig, weighing 400 to 500 g, a portion of skin was unhaired and rubbed lightly with sandpaper, to which 0.1 ml of microconidium suspension of *Trichophyton mentagrophytes* KD-04 ($10^7$ cells/ml) was dropped and the skin surface was infected by rubbing it with a glass rod. The test compound was dissolved in polyethylene glycol 400-ethanol (75:25) so as to give a 1% solution thereof and 0.2 ml of the resultant solution was applied for treatment once a day for 10 days from 3 days after the infection. The animal was killed by etherization 2 days after the last treatment and 10 tissue specimens of skin were cut out from the infected portion and incubated on Sabouraud's agar medium for 7 days. Inhibitory ratio was calculated according to the following formula:

Inhibitory ratio (%)={1-(number of tissue specimens found fungi/total number of tissue specimens)}×100

The results are shown in Table 2. Clotrimazole was used as a control compound.

TABLE 2

| Group | Inhibitory ratio (%) |
|---|---|
| Control (non-treated) | 0 |
| Control (vehicle) | 0 |
| Compound of Example 1 | 98 |
| Clotrimazole | 20 |

(2) Therapeutic effect on cutaneous candidiasis in guinea pigs.

In the back of male Hartley guinea pig, weighing 400 to 500 g, a portion of skin was unhaired, to which 0.1 ml of spore suspension of *Candida albicans* KC-36 ($5\times10^7$ cells/ml) was dropped and the skin surface was infected by rubbing it with a glass rod. To facilitate the infection, prednisolone was subcutaneously administered at 30 mg/kg on one day before the infection, the day of infection and 4 days after the infection. The test compound was dissolved in polyethylene glycol 400-ethanol (75:25) so as to give a 1% solution thereof and 0.2 ml of the resultant solution was applied for treatment once a day for 3 days from 2 days after the infection. The animal was killed by etherization 2 days after the last treatment and 10 tissue specimens of skin were cut out from the infected portion and incubated on CANDIDA GS AGAR 'EIKEN' (EIKEN CHEMICAL CO., LTD.) for 7 days. The inhibitory ratio was calculated according to the above-mentioned formula. The results are shown in Table 3. Clotrimazole was employed as a control compound.

TABLE 3

| Group | Inhibitory ratio (%) |
|---|---|
| Control (non-treated) | 4 |
| Control (vehicle) | 8 |
| Compound of Example 1 | 98 |
| Clotrimazole | 96 |

Based on the above tests 1 and 2, it was found that the compound of the present invention had strong and widely efficacious antifungal action.

3. Acute toxicity test for mice

The compound of Example 1 was dissolved in polyethylene glycol 200 and the resultant solution was applied to a male ICR mouse of 5 weeks old by oral or subcutaneous administration. The results are shown in Table 4.

TABLE 4

| | Number of died mice/ number of tested mice | |
|---|---|---|
| Dose | subcutaneous | oral |
| 1000 mg/kg | 0/3 | 0/3 |
| 500 mg/kg | 0/3 | 0/3 |
| 250 mg/kg | 0/3 | — |
| 125 mg/kg | 0/3 | — |

As shown in the above Table, it is found that the compound of the present invention has low toxicity.

The compounds of the present invention have strong antifungal activity and low toxicity. A fungicide containing the compound of the present invention having the general formula (I) as an effective ingredient can be employed to treat local and generalized mycosis in a mammal including human, which are caused by a fungus, especially such as Candida, Trichophyton, Microsporum, Epidermophyton, Malassezia, Cryptococcus neoformans, Aspergillus, Coccidioides, Paracoccidioides, Histoplasma or Blastomyces. The fungicide containing the compound of the present invention as an effective ingredient is useful not only for treatment for mycosis in human and animals but also as fungicides for agricultural and horticultural use, fungicides for industrial use and the like.

The fungicide containing the compound of the present invention having the general formula (I) as an effective ingredient may comprise the compound alone or may be a mixture of the compound and liquid or solid auxiliary ingredients in preparing a pharmaceutical preparation such as an excipient, a binder and a diluent. The fungicide can be externally applied or orally or parenterally administered. If required, the fungicide may contain other medicament.

In the case of administering the compound as an external preparation, the preparation may be in a dosage form such as a cream, a liquid preparation, an ointment, an oculentum, a suppository, a vaginal suppository, a powder or an emulsion. In preparing the external preparation, there can be used an oily base, an emulsion base or the like. A preferable content of the effective ingredient is 0.1 to 10% by weight. The dosage may suitably vary with an area of an affected part and the symptom.

In case of oral administration, the fungicide is used as a powder, a tablet, a granule, a capsule or a syrup, and further, the fungicide is also used as a injection such as a subcutaneous injection, an intramuscular injection or an intravenous injection.

Although the dosage is different according to the age and body weight of a patient and an individual condition, the dosage is 10 mg to 10 g, preferably about 50 mg to about 5 g as an effective ingredient per day for an adult. With respect to a manner of administration, the compound is administered at the above-mentioned dosage per day in one to several times.

The present invention is more specifically explained by means of the following Examples and Reference Examples. However, it is to be understood that the present invention is not limited to those Examples.

$^1$H-NMR spectra were determined in the solution of deuteriochloroform ($CDCl_3$) using tetramethylsilane as an internal standard by means of JNM-EX270 spectrometer (JEOL LTD.), and a value of chemical shift (δ) was expressed with ppm. The determination by high performance liquid chromatography (hereinafter, referred to as HPLC) was carried out using an chiral column, CHIRALCEL OJ (4.6 mm×25 cm, Daicel Chemical Industries, Ltd.) by means of LC-6A (HPLC apparatus, Shimadzu Corporation).

EXAMPLE 1

(2R,3R)-2-(2,4-difluorophenyl)-3-(4-methylenepiperdine-1-yl)-1-(1H-1,2,4-triazole-1-yl)butane-2-ol There was added 11.2 ml of 50% aqueous solution of potassium hydroxide to 1.336 g of 4-methylenepiperidine hydrochloride and, after dissolved under stirring, the resulting solution was extracted with 20 ml of ethyl ether. Then the aqueous phase was further extracted with 10 ml of ethyl ether, and the organic phases were combined and ethyl ether was removed therefrom. To the residue there were added 3 ml of ethanol, 251 mg of (2R,3S)-2-(2,4-difluorophenyl)-3-methyl-2-[(1H-1,2,4-triazole-1-yl)methyl]oxirane and 3 ml of distilled water in order, and the mixture was refluxed with heating for 24 hours in the oil bath at 85° C. After the reaction, the reaction solution was cooled to room temperature, and thereto were added 20 ml of ethyl acetate and 20 ml of distilled water, and the organic phase was separated. The aqueous phase was further extracted with 10 ml of ethyl acetate, and the organic phase was combined with the above-separated organic phase, and the mixture was washed with a saturated aqueous solution of sodium chloride, and dried over anhydrous magnesium sulfate and then the solvent was removed. The residue was subjected to HPLC using 8 g of silica gel and was eluted with a mixed solvent of ethyl acetate/hexane (4:1 to 3:1) to obtain 188 mg of the titled compound. Yield: 54.0%. Upon recrystallization from a mixed solvent of ether/hexane, a pure product having a melting point of 86°–87° C. was obtained.

HPLC: The analysis was carried out using hexane/isopropyl alcohol of 9/1 as a mobile phase, at a flow rate of 1.0 ml/min at room temperature under the conditions capable of detecting with UV (254 nm), and then a single peak appeared at a retention time of 6.6 minutes.

Specific rotation: $[\alpha]_D^{28}$–93° (C=1.00, $CHCl_3$)

Elemental analysis: For $C_{18}H_{22}F_2N_4O$ Calculated: C,62.15; H, 6.36; N, 16.02 Found: C, 62.05; H, 6.37; N, 16.08

$^1$H-NMR spectrum ($CDCl_3$) δ ppm: 0.96 (3H,dd), 2.1–2.5 (6H,m), 2.6–2.8 (2H,m), 2.91 (1H,q), 4.64 (2H,s), 4.80 (1H,d), 4.89 (1H,d), 5.48 (1H,brs), 6.7–6.8 (2H,m), 7.47–7.63 (1H,m), 7.79 (1H,s), 8.03 (1H,s)

EXAMPLE 2

(2RS,3RS)-2-(2,4-difluorophenyl)-3-(4-methylene-piperdine-1-yl)-1-(1H-1,2,4-triazole-1-yl)butane-2-ol The titled compound was obtained in the same manner as in Example 1 except that instead of (2R,3S)-2-(2,4-difluorophenyl)-3-methyl-2-[(1H-1,2,4-triazole-1-yl) methyl]oxirane, (2RS,3SR)-2-(2,4-difluorophenyl)-3-methyl-2-[(1H-1,2,4-triazole-1-yl)methyl]oxirane being a racemic modification thereof was used.

HPLC: The analysis was carried out using hexane/isopropyl alcohol of 9/1 as a mobile phase, at a flow rate of 1.0 ml/min at room temperature under the conditions capable of detecting with UV (254 nm), and then two peaks having an area ratio thereof of 1:1 appeared at retention times of 6.6 minute and 5.8 minute, respectively.

$^1$H-NMR spectrum ($CDCl_3$) δ ppm: 0.96 (3H,dd, J=3 Hz,7 Hz), 2.1–2.5 (6H, m), 2.6–2.8 (2H,m), 2.91 (1H,q,J=7 Hz), 4.64 (2H,s), 4.80 (1H,d,J=15 Hz), 4.89 (1H,d,J=15 Hz), 5.47 (1H,brs), 6.7–6.8 (2H,m), 7.5–7.6 (1H,m), 7.79 (1H,s), 8.02 (1H,s)

EXAMPLE 3

(2S,3S)-2-(2,4-difluorophenyl)-3-(4-methylene-piperdine-1-yl)-1-(1H-1,2,4-triazole-1-yl)butane-2-ol The titled compound was obtained in the same manner as in Example 1 except that instead of (2R,3S)-2-( 2,4-difluorophenyl)-3-methyl-2-[(1H-1,2,4-triazole-1-yl)methyl]oxirane, (2S,3R)-2-(2,4-difluorophenyl)-3-methyl-2-[(1H-1,2,4-triazole-1-yl)methyl]oxirane being an enantiomer thereof was used.

HPLC: The analysis was carried out using hexane/isopropyl alcohol of 9/1 as a mobile phase, at a flow rate of 1.0 ml/min at room temperature under the conditions capable of detecting with UV (254 nm), and then a single peak appeared at a retention time of 5.8 minutes.

$^1$H-NMR spectrum ($CDCl_3$) δ ppm: 0.96 (3H,dd,J=3 Hz,7 Hz), 2.1–2.5 (6H,m), 2.6–2.8 (2H,m), 2.91 (1H,q,J=7 Hz), 4.64 (2H,s), 4.80 (1H,d,J=15 Hz), 4.89 (1H,d,J=15 Hz), 5.48 (1H,brs), 6.7–6.8 (2H,m), 7.5–7.6 (1H,m), 7.78 (1H,s), 8.03 (1H,s)

EXAMPLES 4 TO 14

The compounds of Examples 4 to 14 shown in Table 6 were synthesized using starting materials shown in Table 5 in the same manner as in Example 1.

TABLE 5

Epoxy compound (II)

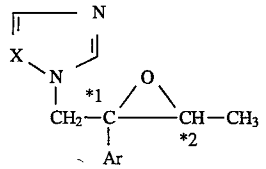

Amine derivative (III)

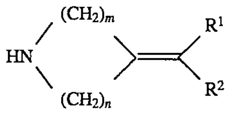

| Ex. No. | X | *1 | *2 | Ar | $R^1$ | $R^2$ | m | n |
|---|---|---|---|---|---|---|---|---|
| 4 | CH | R | S | 2,4-difluorophenyl | H | H | 2 | 2 |
| 5 | CH | RS | SR | 2,4-difluorophenyl | H | H | 2 | 2 |
| 6 | N | R | S | 4-chlorophenyl | H | H | 2 | 2 |
| 7 | N | R | S | 2,4-dichlorophenyl | H | H | 2 | 2 |
| 8 | N | RS | SR | 2,4-difluorophenyl | H | $CH_3$ | 2 | 2 |
| 9 | N | R | S | 2,4-difluorophenyl | H | n-$C_5H_{11}$ | 2 | 2 |
| 10 | N | RS | SR | 2,4-difluorophenyl | H | Ph* | 2 | 2 |
| 11 | N | R | S | 2,4-difluorophenyl | Ph* | Ph* | 2 | 2 |
| 12 | N | R | S | 2,4-difluorophenyl | H | $CH{=}CH_2$ | 2 | 2 |
| 13 | N | R | S | 2,4-difluorophenyl | H | H | 3 | 1 |
| 14 | N | R | S | 2,4-difluorophenyl | H | H | 2 | 1 |

*Ph is phenyl group

TABLE 6

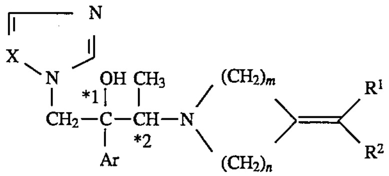

Obtained compound

| Ex. No. | $R^1$ | $R^2$ | X | m | n | Absolute configuration *1 | Absolute configuration *2 | Ar | $^1$H-NMR spectrum ($CDCl_3$) |
|---|---|---|---|---|---|---|---|---|---|
| 4 | H | H | CH | 2 | 2 | R | R | 2,4-difluorophenyl | 1.03 (3H, dd, J=5Hz, 7Hz), 2.2–2.4 (8H, m), 2.77 (1H, q, J=7Hz), 4.35 (1H, d ,J=14Hz), 4.54 (1H, d, J=14Hz), 4.64 (2H, s), 6.7–6.8 (3H, m), 6.92 (1H, s), 7.45 (1H, s), 7.5–7.6 (1H, m) |
| 5 | H | H | CH | 2 | 2 | RS | RS | 2,4-difluorophenyl | 1.02 (3H, dd, J=5Hz, 7Hz), 2.2–2.4 (8H, m), 2.77 (1H, q, J=7Hz), 4.35 (1H, d, J=14Hz), 4.54 (1H, d, J=14Hz), 4.64 (2H, s), 6.7–6.8 (3H, m), 6.92 (1H, s), 7.45 (1H, s), 7.5–7.6 (1H, m) |
| 6 | H | H | N | 2 | 2 | R | R | 4-chlorophenyl | 1.07 (3H, d, J=7Hz), 2.0–2.4 (8H, m), 2.55 (1H, q, J=7Hz), 4.41 (1H, d, J=14Hz), 4.61 (2H, s), 4.70 (1H, d, J=14Hz), 5.80 (1H, s), 7.2–7.5 (4H, m), 7.84 (1H, s), 8.17 (1H, s) |
| 7 | H | H | N | 2 | 2 | R | R | 2,4-dichlorophenyl | 0.80 (3H, d, J=7Hz), 2.2–2.4 (4H, m), 2.4–2.6 (2H, m), 2.9–3.1 (2H, m), 3.55 (1H, q, J=7Hz), 4.66 (2H, s), 4.83 (1H, d, J=15), 4.91 (1H, s), 5.52 (1H, d, J=15Hz), 7.09 (1H, dd, J=9Hz, 2Hz), 7.27 (1H, d, J=2Hz), 7.56 (1H, d, J=9Hz), 7.74 (1H, s), 7.93 (1H, s), 8.04 (1H, s) |
| 8 | H | $CH_3$ | N | 2 | 2 | RS | RS | 2,4-difluorophenyl | 0.97 (3H, dd, J=3Hz, 7Hz), 1.56 (3H, d, J=7Hz), 2.1–2.5 (6H, m), 2.5–2.8 (2H, m), 2.87 (1H, q, J=7Hz), 4.79 (1H, d, J=15Hz), 4.88 (1H, d, J=15Hz), 5.17 (1H, q, J=7Hz), 5.62 (1H, s), 6.7–6.9 (2H, m), 7.27 (1H, s), 7.5–7.6 (1H, m), 7.79 (1H, s), 8.05 (1H, s) |
| 9 | H | $C_5H_{11}$ | N | 2 | 2 | R | R | 2,4-difluorophenyl | 0.88 (3H, t, J=7Hz), 0.97 (3H, dd, J=7Hz, 4Hz), 1.2–1.4 (6H, m), |

TABLE 6-continued

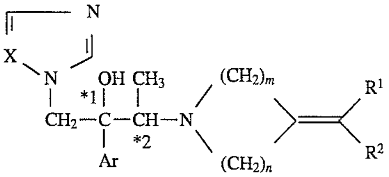

| Ex. No. | $R^1$ | $R^2$ | X | m | n | Absolute configuration *1 | *2 | Ar | $^1$H-NMR spectrum ($CDCl_3$) |
|---|---|---|---|---|---|---|---|---|---|
| | | | | | | | | | 1.9–2.0 (2H, m), 2.1–2.3 (6H, m), 2.6 (2H, m), 2.86 (1H, q, J=7Hz), 4.78 (1H, d, J=15Hz), 4.88 (1H, d, J=16Hz), 5.10 (1H, t, J=7Hz), 5.6 (1H, brs,), 6.7–6.8 (2H, m), 7.3–7.6 (1H, m), 7.79 (1H, s), 8.05 (1H, s) |
| 10 | H | Ph | N | 2 | 2 | RS | RS | 2,4-difluorophenyl | 0.97 (3H, dd, J=3Hz, 7Hz), 1.56 (3H, d, J=7Hz), 2.6–2.7 (1H, m), 2.7–2.8 (1H, m), 2.91 (1H, q, J=7Hz), 4.82 (1H, d, J=15Hz), 4.91 (1H, d, J=15Hz), 5.5 (1H, brs), 6.26 (1H, s), 6.7–6.8 (2H, m), 7.1–7.2 (3H, m), 7.3 (2H, m), 7.5–7.6 (1H, m), 7.79 (1H, s), 8.03 (1H, s) |
| 11 | Ph | Ph | N | 2 | 2 | R | R | 2,4-difluorophenyl | 1.00 (3H, dd, J=7Hz), 2.35 (6H, s), 2.6–2.7 (2H, m), 2.89 (1H, q, J=7Hz), 4.76–4.90 (2H, dd, J=9Hz, 15Hz), 6.7–6.8 (2H, m), 7.1–7.3 (10H, m), 7.5 (1H, m), 7.78 (1H, s), 8.05 (1H, s) |
| 12 | H | $CHCH_2$ | N | 2 | 2 | R | R | 2,4-difluorophenyl | 0.95, 1.01 (3H, each dd, J=3Hz, 7Hz), 1.76 (2H, d), 2.1–2.2 (2H, m), 2.3–2.4 (2H, m), 2.6–2.7 (1H, m), 2.9 (1H, m), 3.0–3.3 (1H, m), 4.6–5.2 (3H, m), 5.51 (1H, brs), 5.4–5.7 (1H, m), 6.82, 6.05 (1H, each d, J=11Hz, 16Hz), 6.7–6.8 (1H, m), 7.5–7.6 (1H, m), 7.78 (1H, s), 8.02 (1H, s) |
| 13 | H | H | N | 3 | 1 | R | R | 2,4-difluorophenyl | 1.02 (3H, dd, J=3.7Hz), 1.5–1.8 (2H, m), 2.0–2.2 (2H, m), 2.3–2.5 (2H, m), 2.6–2.9 (3H, m), 3.15 (1H, d, J=10Hz), 4.65 (1H, s), 4.70 (1H, s), 4.75 (1H, J=15Hz), 5.53 (1H, s), 6.7–6.9 (2H, m), 7.5–7.6 (1H, m), 7.78 (1H,s ), 8.04 (1H, s) |
| 14 | H | H | N | 2 | 1 | R | R | 2,4-difluorophenyl | 0.90 (3H, dd, J=2Hz, 7Hz), 2.43 (2H, brs), 2.7–2.9 (2H, m), 3.2–3.4 (2H, m), 4.81 (1H, d, J=15Hz), 4.86 (1H, d, J=2Hz), 4.90 (1H, d, J=15Hz), 6.7–6.8 (2H, m), 7.4–7.5 (1H, m), 7.77 (1H, s), 7.95 (1H, s) |

EXAMPLE 15

(Another process for synthesizing the compound in Example 1)

There was dissolved 17.59 g (70 mmol) of (2R,3S)-2-(2,4-difluorophenyl)-3-methyl-2-[(1H-1,2,4-triazole-1-yl)methyl]oxirane in 113 g of an aqueous solution of 4-methylenepiperidine (content: 61%) and the obtained solution was refluxed with heating at 90° C. for 21 hours. After the reaction, an excess of 4-methylenepiperidine was removed under reduced pressure, and the residue was dissolved in 140 ml of isopropyl alcohol and thereto was added 13.32 g (70 mmol) of p-toluenesulfonic acid monohydrate dissolved in 50 ml of isopropyl alcohol. The obtained mixture was allowed to stand for 1 hour at room temperature and overnight in a refrigerator, and then the precipitated crystal was separated by filtration and washed with 50 ml of isopropyl alcohol and dried to obtain 32.20 g of (2R,3R)-2-(2,4-difluorophenyl)-3-(4-methylenepiperidine-1-yl)-1-(1H-1,2,4-triazole-1-yl)butane-2-ol p-toluenesulfonate in a form of a crystal.

To 18.3 g of the p-toluenesulfonate obtained above there were added 40 ml of ethyl ether and 35 ml of 1N aqueous solution of sodium hydroxide. The organic phase was taken out, and dried over 5 g of anhydrous magnesium sulfate and then the solvent was removed. There was added 40 ml of n-hexane to the residual liquid, and the precipitated crystal was separated by filtration, and dried to obtain 9.43 g of the desired (2R,3R)-2-(2,4-difluorophenyl)-3-(4-methylenepiperidine-1-yl)-1-(1H-1,2,4-triazole-1-yl)butane-2-ol.

$^1$H-NMR spectrum of this compound coincided with that of the compound in Example 1.

REFERENCE EXAMPLE 1

Synthesis of 4-benzylidenepiperidine hydrochloride (1) In a stream of argon, 49.0 g (126 mmol) of benzyltriphenylphosphonium chloride was suspended in 100 ml of anhydrous tetrahydrofurane, and thereto 86 ml of butyllithium was added dropwise under cooling with ice. After stirring the mixture at room temperature for 1 hour, thereto was added dropwise a solution of 1-benzyl-4-piperidone in anhydrous tetrahydrofurane under cooling with ice and the obtained mixture was refluxed with heating for 15 hours. The reaction solution was filtrated, and diethyl ether and water were added to the filtrate, and the organic phase was taken out. The organic phase was washed with water and a saturated aqueous solution of sodium chloride, and dried over anhydrous magnesium sulfate. The solvent was removed under reduced pressure, and the resulting oily matter was subjected to a column chromatography using 1 kg of silica gel and eluted with ethyl acetate-hexane (1:100 to 3:100) to obtain 22.6 g of 1-benzyl-4-benzylidenepiperidine.

$^1$H-NMR spectrum ($CDCl_3$) δ ppm: 2.4–2.5 (4H,m), 2.5–2.6 (4H,m), 3.52 (2H,s), 6.27 (1H,s), 7.1–7.4 (10H,m)

(2) There was dissolved 24.6 g (96 mmol) of 1-benzyl-4-benzylidenepiperidine in 200 ml of dichloroethane and thereto 11.1 ml (102 mmol) of 1-chloroethyl chloroformate was added dropwise under cooling with ice. The reaction solution was refluxed with heating for 30 minutes and then stirred at room temperature for 1.5 hours. The reaction solution was concentrated to 80 ml by removing the solvent under reduced pressure, thereto was added 200 ml of methanol and the obtained mixture was refluxed with heating for 12 hours. The solvent was removed under reduced pressure and to the obtained residue was added 100 ml of isopropyl ether and the precipitate was separated by filtration to obtain 8.6 g of the titled compound.

$^1$H-NMR spectrum ($CDCl_3$) δ ppm: 2.74 (2H,t,J=6 Hz), 2.84 (2H,t,J=6 Hz), 3.18 (2H,brs), 3.31 (2H,brs), 6.47 (1H, s), 7.1–7.4 (5H,m), 9.8 (2H,brs)

REFERENCE EXAMPLE 2

Synthesis of 4-diphenylmethylenepiperidine (1) There was suspended 102 g (650 mmol) of ethyl isonipecotate in 100 ml of dioxane. Under cooling with ice, thereto was added 213 g (974 mmol) of t-butoxydicarbamate, and the obtained mixture was stirred for 15 hours. The solvent was removed under reduced pressure and 234 g of 1-t-butoxycarbonyl-4-ethoxycarbonylpiperidine was obtained.

$^1$H-NMR spectrum ($CDCl_3$) δ ppm: 1.27 (3H,t,J=7 Hz), 1.46 (9H,s), 1.6–1.7 (2H,m), 1.8–1.9 (2H,m), 2.3–2.5 (1H, m), 2.8–2.9 (2H,m), 3.7–4.0 (2H,m), 4.14 (2H,q,J=7 Hz)

(2) In a stream of argon, 26.4 g (72 mmol) of 1-t-butoxycarbonyl-4-ethoxycarbonylpiperidine was dissolved in 100 ml of dry tetrahydrofuran, and under cooling with ice, thereto 108 ml of 2 mol/ml phenylmagnesium bromide was added dropwise and the obtained mixture was stirred for 2 days. The reaction solution was poured into 200 ml of a saturated solution of ammonium chloride and 200 ml of ethyl acetate, and the organic phase was taken out. The organic phase was washed with water and a saturated aqueous solution of sodium chloride, and dried over anhydrous magnesium sulfate. The solvent was removed under reduced pressure and 34.7 g of 1-t-butoxycarbonyl-4-(hydroxydiphenyl)methylpiperidine was obtained.

$^1$H-NMR spectrum ($CDCl_3$) δ ppm: 1.2 (4H,m), 1.42 (9H,s), 2.5–2.7 (3H,m), 4.1–4.2 (2H,m), 7.2–7.5 (10H,m)

(3) There was dissolved 20 g (54 mmol) of 1-t-butoxycarbonyl-4-(hydroxydiphenyl)methylpiperidine in 12.8 g of phenol and 210 ml of 48% aqueous solution of hydrogen bromide, and the obtained solution was stirred at 140° C. for 5 hours and at room temperature for 15 hours. The organic phase was taken out, and thereto was added diethyl ether and then the resulting precipitate was separated by filtration. To the precipitate was added diethyl ether and an aqueous solution of potassium hydroxide, and the organic phase was taken out and dried over potassium hydroxide. The solvent was removed under reduced pressure and 6.1 g of the titled compound was obtained.

$^1$H-NMR spectrum ($CDCl_3$) δ ppm: 2.0 (1H,brs), 2.32 (4H,t,J=6 Hz), 2.9 (4H,t,J=6 Hz), 7.1–7.3 (10H,m)

REFERENCE EXAMPLE 3

Synthesis of 4-propenylidenepiperidine hydrochloride (1) In a stream of argon, 2.9 g (7.5 mmol) of allyltriphenylphosphonium bromide was suspended in 10 ml of anhydrous tetrahydrofurane, and thereto 4.3 ml of butyllithium was added dropwise under cooling with ice. After stirring the mixture at room temperature for 30 minutes, thereto was added dropwise a solution of 1 g (5.3 mmol) of 1-benzyl-4-piperidone in anhydrous tetrahydrofurane under cooling with ice and the obtained mixture was stirred at room temperature for 15 hours. The reaction solution was filtrated, and ethyl acetate and water were added to the filtrate, and the organic phase was taken out. The organic phase was washed with water and a saturated aqueous solution of sodium chloride, and dried over anhydrous magnesium sulfate. The solvent was removed under reduced pressure, and the resulting oily matter was subjected to a column chromatography using 40 g of silica gel and eluted with ethyl acetate-hexane (1:1 to 1:3 ) to obtain 200 mg of 1-benzyl-4-propylidenepiperidine.

$^1$H-NMR spectrum ($CDCl_3$) δ ppm: 2.2–2.3 (2H,m), 2.4–2.5 (6H,m), 3.50 (2H,s), 4.98 (1H,d,J=10 Hz), 5.11 (1H,d,J=17 Hz), 5.82 (1H,d,J=11 Hz), 6.5–6.6 (1H,m), 7.2–7.3 (5H,m)

(2) There was dissolved 4.5 g (21 mmol) of 1-benzyl-4-propylidenepiperidine in 20 ml of dichloroethane and thereto 2.8 ml (25 mmol) of 1-chloroethyl chloroformate was added dropwise under cooling with ice. The reaction solution was stirred at room temperature for 30 minutes and then refluxed with heating for 30 minutes. The reaction solution was concentrated to 10 ml by removing the solvent under reduced pressure, and thereto was added 60 ml of methanol and the obtained mixture was refluxed with heating for 12 hours. The solvent was removed under reduced pressure to obtain 3.7 g of the titled compound.

$^1$H-NMR spectrum ($CDCl_3$) δ ppm: 2.3–3.0 (4H,m), 3.0–3.6 (4H,m), 4.7–6.3 (4H,m)

PHARMACEUTICAL PREPARATION EXAMPLE 1

Liquid preparation

There was dissolved 200 ml of macrogol 400 in 750 ml of ethanol, and thereto was added 5 g of (2R,3R)-2-(2,4-difluorophenyl)-3-(4-methylenepiperidine-1-yl)-1-(1H-1,2,4-triazole-1-yl)butane-2-ol being the compound in Example 1 and dissolved. Then, the total volume thereof was made to 1000 ml with ethanol and the obtained liquid was used as a liquid preparation.

PHARMACEUTICAL PREPARATION EXAMPLE 2

Ointment

A mixture comprising 400 g of white soft paraffine, 180 g of cetanol, 1 g of propyl p-hydroxybenzoate and 50 g of sorbitan sesquioletate was melted on a water bath with keeping the temperature thereof at 80° C. Then 5 g of (2R,3R)-2-(2,4-difluorophenyl)-3-(4-methylenepiperidine-1-yl)-1-(1H-1,2,4-triazole-1-yl)butane-2-ol being the compound in Example 1, was added thereto and dissolved. To the above-mentioned liquid, a liquid which was obtained by adding water to 1 g of methyl p-hydroxybenzoate and heating the mixture to 80° C. to melt it, was gradually added and mixed them. After cooling the mixture, the obtained matter was used as an ointment.

PHARMACEUTICAL PREPARATION EXAMPLE 3

Cream

A mixture comprising 15 g of white soft paraffin, 200 g of liquid paraffin, 50 g of stearyl alcohol, 40 g of glyceryl monostearate, 145 g of propylene glycol and 1 g of propyl p-hydroxybenzoate was melted on a water bath with keeping the temperature thereof at 80° C. Then 10 g of (2R,3R)-2-(2,4-difluorophenyl)-3-(4methylenepiperdine-1-yl)-1-(1H-1,2,4-triazole-1-yl)butane-2-ol being the compound in Example 1, was added thereto and dissolved. To the obtained solution was added a solution which was obtained by adding 498 g of purified water to 40 g of polyoxyl 40 stearate and 1 g of methyl p-hydroxybenzoate and heating the obtained mixture to 80° C. to melt it, and then the obtained mixture was stirred thoroughly. After stirring, the mixture was further stirred thoroughly under cooling with cooled water to become solid and then used as a cream.

INDUSTRIAL APPLICABILITY

The compounds of the present invention have a strong antifungal activity. Therefore the fungicide containing the compound of the present invention having the general formula (I) as an effective ingredient, is effective for preventing and treating mycosis in human and animals, and also useful as fungicides for agricultural and horticultural use, fungicides for industrial use, and the like.

We claim:

1. A compound having the formula (I):

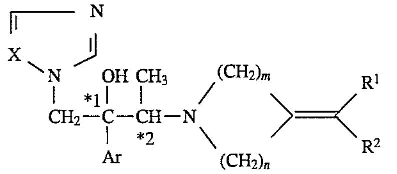

(I)

wherein

Ar is non-substituted phenyl group or a phenyl substituted with 1 to 3 substituents selected from a halogen atom and trifluoromethyl, $R^1$ and $R^2$ are the same or different and are hydrogen atom, a lower alkyl group of 1 to 6 carbon atoms, a non-substituted phenyl, naphthyl or biphenyl group, a phenyl, naphthyl or biphenyl group substituted with 1 to 3 substituents selected from a halogen atom, a lower alkyl group of 1 to 6 carbon atoms, a trifluoromethyl group and a nitro group, an alkenyl group of 2 or 3 carbon atoms, an ethynyl group, a styryl group, a benzyl group, a naphthylmethyl group or a 4-nitrobenzyl group, m is 2 or 3, n is 1 or 2, X is nitrogen atom, and

*1 and *2 mean an asymmetric carbon atom, or an acid addition salt thereof.

2. The compound or the acid addition salt thereof of claim 1 wherein an absolute configuration of the asymmetric carbon atoms with *1 and *2 is R,R-configuration.

3. The compound or the acid addition salt thereof of claim 1 which is a mixture containing the compound having the formula (I) wherein the absolute configuration of the asymmetric carbon atoms with *1 and *2 is R,R-configuration or an acid addition salt thereof and other optical isomer.

4. The compound or the acid addition salt thereof of claim 2 or 3 wherein the compound having the formula (I) wherein the absolute configuration of the asymmetric carbon atoms with *1 and *2 is R,R-configuration, is (2R,3R)-2-(2,4-difluorophenyl)-3-(4-methylenepiperidine-1-yl)-1-(1H-1,2,4-triazole-1-yl)-butane-2-ol.

5. A fungicide composition comprising an antifungal effective amount of the compound or the acid addition salt thereof of claim 1.

6. A fungicide composition comprising an antifungal effective amount of the compound or the acid addition salt thereof of claim 2.

7. A fungicide composition comprising an antifungal effective amount of the compound or the acid addition salt thereof of claim 3.

8. A fungicide composition comprising an antifungal effective amount of the compound or the acid addition salt thereof of claim 4.

9. A process for treating mycosis comprising administering to a subject in need thereof an effective amount of the compound or the acid addition salt thereof of claim 1.

10. A process for treating mycosis comprising administering to a subject in need thereof an effective amount of the compound or the acid addition salt thereof of claim 2.

11. A process for treating mycosis comprising administering to a subject in need thereof an effective amount of the compound or the acid addition salt thereof of claim 3.

12. A process for treating mycosis comprising administering to a subject in need thereof an effective amount of the compound or the acid addition salt thereof of claim 4.

* * * * *

UNITED STATES PATENT AND TRADEMARK OFFICE

CERTIFICATE OF CORRECTION

PATENT NO. : 5,620,994
DATED : April 15, 1997
INVENTOR(S) : Naito et al.

It is certified that error appears in the above-identified patent and that said Letters Patent is hereby corrected as shown below:

Column 2,
Lines 48-49, 50-51, 52-53, 54-55, 56-57, 58-59, 60-61, 62-63, 64-65 and 66-67, "4-methylenepiperidine-1-yl" should be -- 4-methylenepiperidino --.
Lines 49, 51, 53, 61, 63 and 65, "1H-1,2,4-triazole-1-yl" should be -- 1H-1,2,4-triazol-1-yl --.
Lines 49, 51, 53, 55, 57, 59, 61, 63, 65 and 67, "butane-2-ol" should be -- butan-2-ol --.
Lines 55, 57, 59 and 67, "1H-imidazole-1-yl" should be -- 1H-imidazol-1-yl --.

Column 3,
Lines 1-2, 3-4, 5-6, 7-8, 9-10, 11-12, 13-14, 15-16, 17-18, 19-20, 21-22, 23-24, 25-26, 27-28, 29-30, 31-32, 33-34, 35-36, 37-38, 39,40, 41-42, 43-44, 45-46, 47-48, 49-50, 51-52, 53-54, 55-56 and 57-58, "4-methylenepiperidine-1-yl" should be -- 4-methylenepiperidino --.
Lines 2, 4, 12, 14, 24, 26 and 28, "1H-imidazole-1-yl" should be -- 1H-imidazol-1-yl --.
Lines 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 63, 65 and 67, "butane-2-ol" should be -- butan-2-ol --.
Line 6, 8, 10, 18, 20, 22, 30, 32, 34, 36, 38, 40, 42, 44, 46, 48, 50, 52, 54, 56, 58, 60, 63, 65 and 67, "1H-1,2,4-triazole-1-yl" should be -- 1H-1,2,4-triazol-1-yl --.
Lines 60, 63 and 67, "piperdine-1-yl" should be -- piperidino --.

Column 4,
Line 2, "piperdine-1-yl" should be -- piperidino --.
Lines 2, 4, 6, 8, 10, 12, 14, 16, 18, 20, 22, 24, 26, 28, 30, 32, 34, 36, 38, 40, 42, 44 and 46, "1H-1,2,4-triazole-1-yl" should be -- 1H-1,2,4-triazol-1-yl --.
Lines 2, 4, 6, 8, 10, 12, 14, 16, 18, 20, 22, 24, 26, 28, 30, 32, 34, 36, 38, 40, 44 and 46, "butane-2-ol" should be -- butan-2-ol --.
Lines 3-4, "4-cyclohexylmethylenepiperdine-1-yl" should be -- 4-cyclohexylmethylenepiperidino --.
Lines 5-6, 7-8 and 9-10, "4-benzylidenepiperdine-1-yl" should be -- benzylidenepiperidino --.
Lines 11-12,13-14 and 15-16, "4-isopropylidenepiperdine-1-yl" should be -- 4-isopropylidenepiperidino --.
Lines 17-18, 19-20, 21-22, 23-24, 25-26, 27-28, 29-30, 31-32 and 33-34, "4-diphenylmethylenepiperdine-1-yl" should be -- 4-diphenylmethylenepiperidino --.
Lines 35-36, 37-38, 39-40, 41-42, 43 and 44-46, "3-methylenepiperidine-1-yl" should be -- 3-methylenepiperidino --.

UNITED STATES PATENT AND TRADEMARK OFFICE
CERTIFICATE OF CORRECTION

PATENT NO. : 5,620,994 
DATED : April 15, 1997
INVENTOR(S) : Naito et al.

It is certified that error appears in the above-identified patent and that said Letters Patent is hereby corrected as shown below:

Column 9,
Lines 59-60, "4-methylenepiperdine-1-yl" should be -- 4-methylenepiperidino --.
Line 60, "1H-1,2,4-triazole-1-yl" should be -- 1H-1,2,4-triazol-1-yl --.
Line 60 "butane-2-ol" should be -- butan-2-ol --.

Column 10,
Lines 3, 41, 60 and 64, "1H-1,2,4-triazole-1-yl" should be -- 1H-1,2,4-triazol-1-yl --.
Lines 36-37 and 59-60, "4-methylenepiperdine-1-yl" should be -- 4-methylenepiperidino --.
Line 37, "1H-1,2,4-triazole-1-yl" should be -- 1H-1,2,4-triazol-1-yl --.
Lines 37 and 60, "butane-2-ol" should be -- butan-2-ol --.
Lines 43 and 65, "1,2,4-triazole-1-yl" should be -- 1H-1,2,4-triazol-1-yl --.

Column 13,
Line 56, "1H-1,2,4-triazole-1-yl" should be -- 1H-1,2,4-triazol-1-yl --.

Column 14,
Lines 51 and 61-62, "4-methylenepiperidine-1-yl" should be -- 4-methylenepiperidino --.
Line 52, "4-triazole-1-yl" should be -- 4-triazol-1-yl --.
Lines 52 and 62, "butane-2-ol" should be -- butan-2-ol --.
Line 62, "1H-1,2,4-triazole-1-yl" should be -- 1 H-1,2,4-triazol-1-yl --.

Column 16,
Line 65, "4-methylenepiperidine-1-yl" should be -- 4-methylenepiperidino --.
Line 66, "4-triazole-1-yl" should be -- 4-triazol-1-yl --.
Line 66, "butane-2-ol" should be -- butan-2-ol --.

Column 17,
Lines 12-13, "4-methylenepiperidine-1-yl" should be -- 4-methylenepiperidino --.
Lines 13 and 31, "1H-1,2,4-triazole-1-yl" should be -- 1H-1,2,4-triazol-1-yl --.
Lines 13 and 32, "butane-2-ol" should be -- butan-2-ol --.
Line 31, "4methylenepiperidine-1-yl" should be -- 4-methylenepiperidino --.

UNITED STATES PATENT AND TRADEMARK OFFICE
CERTIFICATE OF CORRECTION

PATENT NO. : 5,620,994
DATED : April 15, 1997
INVENTOR(S) : Naito et al.

It is certified that error appears in the above-identified patent and that said Letters Patent is hereby corrected as shown below:

Column 18,
Line 32, "4-methylenepiperidine-1-yl" should be -- 4-methylenepiperidino --.
Line 33, "4-triazole-1-yl" should be -- 4-triazol-1-yl --.
Line 33, "butane-2-ol" should be -- butan-2-ol --.

Signed and Sealed this

Twenty-second Day of March, 2005

JON W. DUDAS
*Director of the United States Patent and Trademark Office*